(12) United States Patent
Forster (10) Patent No.: US 9,012,850 B2
(45) Date of Patent: Apr. 21, 2015

(54) METHOD AND APPARATUS FOR FILTER CONDITION INSPECTION

(75) Inventor: Peter Ivan Forster, Gainsborough (GB)

(73) Assignee: Ceramex Ltd., Gainsborough Lincolnshire (GB)

( * ) Notice: Subject to any disclaimer, the term of this patent is extended or adjusted under 35 U.S.C. 154(b) by 79 days.

(21) Appl. No.: 13/821,317

(22) PCT Filed: Sep. 20, 2011

(86) PCT No.: PCT/IB2011/054121
§ 371 (c)(1),
(2), (4) Date: Apr. 2, 2013

(87) PCT Pub. No.: WO2012/038894
PCT Pub. Date: Mar. 29, 2012

(65) Prior Publication Data
US 2013/0181134 A1 Jul. 18, 2013

(30) Foreign Application Priority Data
Sep. 20, 2010 (GB) .................................. 1015690.9

(51) Int. Cl.
*G01J 5/02* (2006.01)
*G01N 21/94* (2006.01)
*F01N 3/022* (2006.01)
*F01N 3/027* (2006.01)
*F01N 3/028* (2006.01)
*F01N 3/035* (2006.01)
*F01N 9/00* (2006.01)
(Continued)

(52) U.S. Cl.
CPC .............. *G01N 21/94* (2013.01); *F01N 3/0222* (2013.01); *F01N 3/027* (2013.01); *F01N 3/028* (2013.01); *F01N 3/035* (2013.01); *F01N 9/002* (2013.01); *F01N 13/008* (2013.01); *G01N 25/72* (2013.01); *F01N 11/002* (2013.01); *F01N 2330/06* (2013.01); *F01N 2390/00* (2013.01); *F01N 2550/04* (2013.01); *G01N 22/02* (2013.01); *Y02T 10/47* (2013.01)

(58) Field of Classification Search
CPC ............................... G01N 25/72; G01N 21/71
USPC .................................... 250/340, 341.1–341.8
See application file for complete search history.

(56) References Cited

U.S. PATENT DOCUMENTS 5,292,195 A * 3/1994 Crisman, Jr. ...................... 374/4
5,311,023 A 5/1994 Means, Jr. et al.
(Continued)

FOREIGN PATENT DOCUMENTS

DE  100 53 112    5/2002
EP  1 650 555     4/2006
(Continued)

*Primary Examiner* — Kiho Kim
(74) *Attorney, Agent, or Firm* — Burr & Brown, PLLC (57) ABSTRACT

A method of inspecting a ceramic wall-flow filter (1) for a vehicle exhaust system includes the steps of: a) providing a source (9) of heat energy suitable for heating material within the filter (1); b) applying heat energy from the source (9) to a first end (10) of the filter (1) to heat material within the filter; c) detecting infrared radiation (18) which has been emitted by heated material in the filter using a radiation detector (19) at the second end (11) of the filter (1) to form an image (24) of a pattern of emitted radiation, the pattern of emitted radiation providing an indication of the condition of the filter (1). Another aspect of the invention provides apparatus for use in the method.

19 Claims, 9 Drawing Sheets

(51) Int. Cl.
  *F01N 13/00*     (2010.01)
  *G01N 25/72*     (2006.01)
  *F01N 11/00*     (2006.01)
  *G01N 22/02*     (2006.01)

(56) References Cited

U.S. PATENT DOCUMENTS 5,417,494 A    5/1995    Kempa et al.

2006/0086912 A1    4/2006    Weir et al.
2009/0120062 A1    5/2009    Bardon et al.

FOREIGN PATENT DOCUMENTS

| EP | 1 778 956 | | | 5/2007 | |
| JP | 3 039644 | | | 2/1991 | |
| JP | 11128639 A | * | 5/1999 | | |
| JP | 11166910 A | * | 6/1999 | | G01N 25/72 |
| WO | 2006/016117 | | | 2/2006 | |

* cited by examiner

METHOD AND APPARATUS FOR FILTER CONDITION INSPECTION

The invention relates to a method and apparatus for inspecting the condition of a ceramic wall-flow filter for a vehicle exhaust system. The invention is particularly applicable to the inspection of filters such as continuously regenerating diesel particulate filters (CR-DPFs).

Modern diesel powered vehicle exhaust systems are often provided with filters for removing particulate matter from the vehicle's exhaust stream. These are typically wall-flow filters which are cylindrical ceramic monoliths having elongate channels running along their length, parallel to the axis of the cylinder. The channels are alternately plugged at their ends such that gas entering a channel at one end cannot exit the same channel at its other end. To exit, the gas must pass from one channel to the next through the porous walls of the filter. In so doing, the soot and ash within the gas is trapped on the walls of the filter.

A preferred filter for a modern diesel exhaust system is a continuously regenerating diesel particulate filter, in which exhaust heat and gases from the engine are used to cause the particulate matter to burn off the filter, thereby regenerating the filter.

The above-described wall-flow filters can become contaminated with soot and ash in the course of their operation on heavy-duty diesel-powered vehicles. Under normal conditions at elevated operating temperatures such filters regenerate themselves and effectively self-clean, by soot being burnt out of the filter. However, under adverse conditions, for example where the vehicle undertakes a large amount of city driving where high temperatures of exhaust gases are not reached, or after prolonged use, the filter can become blocked. Once the filter is blocked, even locally, it can be damaged by the heat generated from the exothermic reaction of carbon with oxygen. When severe reactions occur the integrity of the filter is damaged and its effectiveness reduced. One way to prevent this is through a regular maintenance regime which includes periodic, typically annual, cleaning.

As part of the servicing and cleaning regime, it is desirable to assess the condition of the filter prior to and after cleaning to identify imperfect cleaning and potential flaws or damage which might cause the filter to be unfit for use. WO 2006/016117 describes a method and apparatus for carrying out an inspection of filter condition. The method involves transmitting electromagnetic radiation through the filter, and detecting the transmitted radiation to form an image of a pattern which provides an indication of the condition of the filter. The image includes shades of colour or tone representing varying extents of transmission of radiation through different parts of the filter. We have found that this method works well on filters of ceramic materials such as cordierite. However, we have found that the method does not work well with other filter materials such as silicon carbide, where even clean filters transmit very little light. This is surprising because silicon carbide exhibits high transmission of light of wavelength in the range about 550-750 nm, so inspection using light in this wavelength range would be expected to be successful. We have also found that the prior art method is ineffective for filters in which the ceramic material is provided with a catalytic coating, typically by dipping it into a slurry of insoluble particles such as alumina interspersed with metal and then drying it off.

The way in which filters operate in service generally results in ash consolidating at the bottom of the cell against the end plugs on the outlet face. It follows that the most difficult area of a cell to clean is that portion just behind the end plug. Therefore in practice when complete cleaning is not achieved, blockage is generally found in at the bottom of the cell against the end plug. This blockage is typically quite short in length and generally under 50 mm. The light inspection system has proved very successful at showing these blockages and providing a 2D image for analysis. However, knowing the number or percentage of cells with blockage does not provide a complete picture of filter condition. For example, a filter with 50% blocked cells where cells are blocked to 5% of their depth would only have 2.5% of its volume or surface area lost. The image would indicate a failure but in reality the filter could be expected to perform adequately in service.

SUMMARY OF THE INVENTION

Aspects of the invention are specified in the independent claims. Preferred features are specified in the dependent claims.

We have surprisingly found that the condition of a ceramic wall-flow filter for a vehicle exhaust system may be determined by inspection of one end of the filter after applying a source of heat energy to the other end, even when the filter substantially does not transmit infrared radiation through both ends.

The term 'heat energy' is used herein to refer to infrared electromagnetic radiation and also to other radiation which is absorbed by material in the filter to produce heat; for example microwave radiation, depending on the nature and composition of the filter. The term also encompasses use of a heat source directly applied to the end face of a filter, for example a hotplate, water bath, or heated metal block, which may heat the end face by direct conduction of heat in addition to radiation of infrared wavelengths.

When a suitable source of heat energy is applied to one end, initially no detail can be seen when viewed from the other end using a suitable infrared detector. Over time, however, as heat energy is absorbed by material in the filter, the material heats up and emits a pattern of radiation from open channels in the filter, the pattern of radiation being emitted depending on the depth of blockages within the channels.

Preferably, the image of the pattern of emitted radiation includes shades of colour or tone representing varying extents of emission of infrared radiation through different parts of the filter. The image may include a range of different colours or tones, each colour or tone representing a different amount of emitted radiation. Preferably, the image includes at least 10 different colours or tones and most preferably, the image contains at least 200 different colours or tones.

The method is particularly applicable to inspecting diesel particulate filters. The wall-flow filter includes elongate channels running from one end to its opposite end, along its length, the channels being alternately plugged at their ends so that gas entering a channel at one end cannot exit the same channel at the opposite end, but instead must pass from one channel to the next through the porous filter material. Such filters are typically cylindrical, including a central axis which is parallel to the length of the channels but may be of other cross sectional shapes. The porous material of such filters is typically crystalline, and may for example comprise cordierite, silicon carbide or aluminium titanate.

The present invention offers the possibility of gaining a measurement of the depth of blockage. This seems most achievable when the blockages are in contact with the end plugs at the hot face of the filter and the blockage length is relatively short. It would appear that when these conditions are met, heat is able to conduct through the ash in sufficient amount and time to provide a rapid detectable change in contrast against the background. As the surfaces within the filter become warmer they too radiate heat. This re-radiation of heat appears to outpace conduction once the hot face temperature builds and this steadily reduces contrast across the whole filter. Heavily blocked cells remain in high contrast for much longer but detecting the amount of blockage becomes more difficult.

Blockage that occurs away from the hot face is usually associated with exothermic damage. These areas remain in high contrast for a good period of time, but are most easily identified by their size shape and tendency to contain holes that can align and allow radiation to pass directly to the detector (bright spots).

Preferably the heat is applied as electromagnetic radiation and is applied uniformly to an end of the filter, rather than being pulsed.

Any suitable heat source may be used. The source may, for example, provide infrared or microwave radiation. For convenience the invention will be described with reference to use of infrared radiation as a heat source, but it will be understood that the invention is not limited to this embodiment. For example the source of heat energy could be a hotplate, preferably of the same shape and dimensions as the face of the filter to which it is to be applied. In one embodiment, the heat source is one or more lamps which emit infrared radiation. Alternatively or additionally, the method may include the use of one or more laser diodes or high power LEDs.

The method may include the step of providing an array of radiation sources such that radiation is provided for simultaneous application to the whole of one end of the filter. Alternatively, a single radiation source or an array of radiation sources insufficient to provide radiation for heating the entire face of a filter may be provided and the method may include the step of moving these radiation sources to scan over the entire end of the filter.

The radiation detector may be an infrared camera to detect the pattern of emitted radiation and form the image. The camera may include an array of charge-coupled devices (CODs), ferro-electric detectors, micro bolometer and MCT arrays.

The method may include the use of a complementary metal-oxide semi-conductor (CMOS) array camera for detecting the pattern of transmitted radiation and forming the image. The camera may produce an image comprising an array of pixels, at least one pixel being provided for each channel of the filter. Preferably, at least 25 pixels, and most preferably at least 90 pixels, are provided for each channel of the filter.

Alternatively, the method may include the use of a focal plane array detector for detecting the pattern of radiation and forming the image. Such a detector is sensitive to radiation with a wavelength of between 700 and 1400 nm, i.e. infrared radiation.

The method may include the use of an array of detectors for simultaneously detecting radiation emitted from substantially the entire area of a face of the filter. Alternatively, the method may include the use of a single radiation detector, which is moved over the filter to sequentially detect radiation which has been emitted from different parts of the filter. Alternatively, the method may include the use of a linear array of detectors, which are moved in one dimension only over the end of the filter, preferably in a direction perpendicular to the length of the array, to sequentially detect radiation emitted from different parts of the filter.

The method may include the use of an array of radiation detectors mounted on an arm which has one of its ends mounted on a pivot. Where the filter is cylindrical, the pivot may coincide with the central axis of the filter.

The method may include rotation of the pivot to sweep the detectors over the whole of the end of the filter. The heat source may be of a fixed type covering the whole of the opposite end of the filter or may be moved in a synchronised manner with the detector.

The method may further include the step of analysing the image of the pattern of emitted radiation to provide an indication of the condition of the filter. The analysis may be carried out visually, by inspecting a visual image of the emitted radiation. Alternatively, the method may include the use of a processor to analyse an image of the emitted radiation.

In a preferred embodiment, a plurality of images are taken over a time interval, and these images are used to determine the location, position, and extent of a blockage in a given channel or region of the filter.

The analysis may include a comparison of the image of the emitted radiation with an image of emitted radiation for an equivalent undamaged filter. The undamaged filter could be theoretical or the image could be produced by carrying out the method with a filter which is known to be undamaged.

The analysis may include a comparison of the image of the emitted radiation with an image of emitted radiation for a filter which just passed a suitability test and/or a filter which just failed a suitability test.

The analysis may include analysing individual cells or groups of cells in the image, each cell corresponding with a channel in the filter.

The comparison may include checking for areas of the filter in which the image shows that more or less radiation has been emitted from the filter being inspected than would be emitted by the undamaged filter.

The relative brightness and darkness of different areas of the image may be analysed.

It is desirable that the heat source will provide sufficient energy to conduct evaluation of the filter in less than one minute. The time required to obtain an image of adequate contrast is not only dependent on the distance between the source and the hot face of the filter and the type and power of heat applied, but is also affected by the type of material used to form the monolith, the amount and position of ash within the filter and the moisture content of the filter. When the source of heat is initially applied to the first end of the filter, no image is visible at the second end. This contrasts with prior art test methods, in which electromagnetic waves are transmitted through the filter to achieve an instantaneous image. Under our current test arrangement an image starts to develop after 10 to 15 seconds of heating and good contrast is usually achieved with a heating time of 30 to 60 seconds. Our calculations suggest that a minimum power output of $10 \text{ kW} \cdot \text{m}^{-2}$ should preferably be used. The maximum radiant emittance or radiosity is not critical and will depend on how close the heat source is to the first end; providing the heat source does not heat the filter sufficiently to cause exothermic damage, any higher power output may be used, for example 10 to 20 $\text{kW} \cdot \text{m}^{-2}$, or even $30 \text{ kW} \cdot \text{m}^{-2}$ or more. We calculate that 10 to $20 \text{ kW} \cdot \text{m}^{-2}$ will be sufficient to raise the filter face material to a suitable temperature, typically 20° C. or more above ambient, within a time period of 30-60 s for a range of ceramic filters.

We intend to use a thermal imaging camera with 320×240 resolution Thus generating 76800 pixels. Our smallest sensible field of view would need to be around 14×10.5 inches (356×267 mm) giving an objective area of around 150 sq inches (96774 mm$^2$).

Currently we foresee monoliths with between 50 and 250 (open) cells/inch² (7.75 and 38.75 open cells/cm² or 100 to 500 (total) cells/inch² (15.5 to 77.5 cells/cm²).

150×100 cpi=15000 cells in field of view
150×200 cpi=30000 cells in field of view
150×300 cpi=45000 cells in field of view
150×400 cpi=60000 cells in field of view
150×500 cpi=75000 cells in field of view Therefore in theory we should have between 1 & 5 pixels per cell dependent on the number of cpi.

In practice images of filters with 100 cpi (3.94 cells/mm) are reasonable, it being possible to make out even the cell walls to some extent. However, at 400 cpi (15.75 cells/mm) the definition of some cells is lost and the image starts to show interference fringes and patterns. However, as each blocked cell is always surrounded by 4 closed cells, a single blocked cell still presents a detectable dark contrast area even on the higher cell-density monoliths.

We believe that good statistical analysis of the image will be possible on monoliths with high cell density, particularly if photo enhancement techniques are used. A line scanning image capture system may become an option should developments result in a commercially available array of sufficient size, definition and sensitivity.

BRIEF DESCRIPTION OF THE DRAWINGS

The invention will now be further described, by way of example only, with reference to the following drawings, in which.

DETAILED DESCRIPTION

Figure 1:
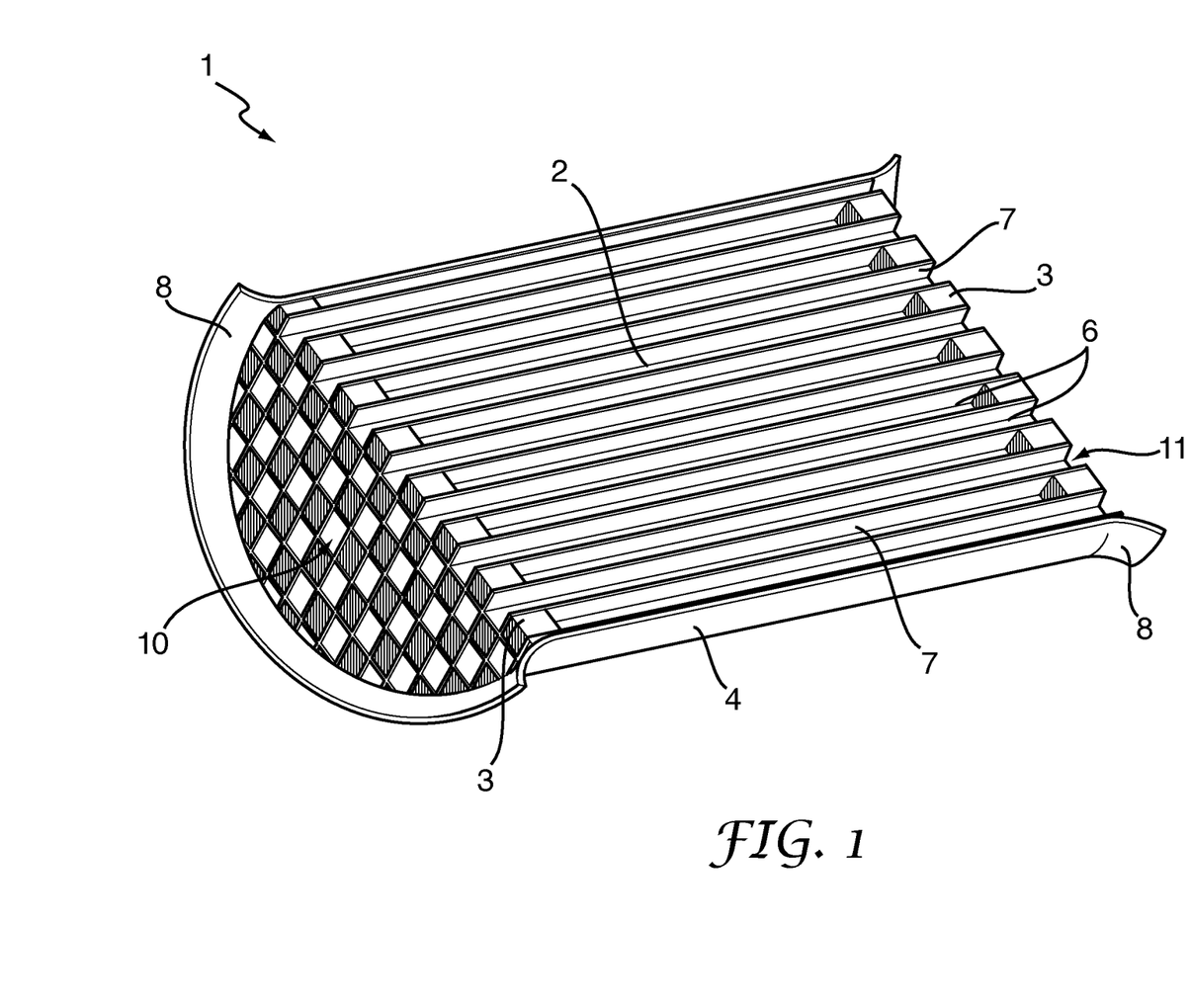
FIG. 1 shows a partial perspective diagram of a wall-flow filter such as a continuously regenerating diesel particulate filter (CR-DPF)
Figure 2:
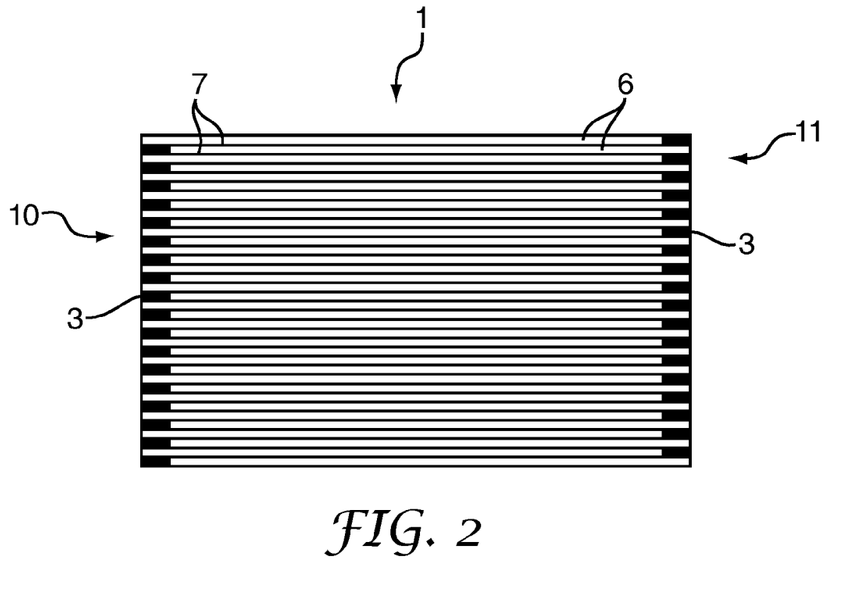
FIG. 2 is a diagrammatic sectional illustration of the wall-flow filter of FIG. 1.
Figure 3:
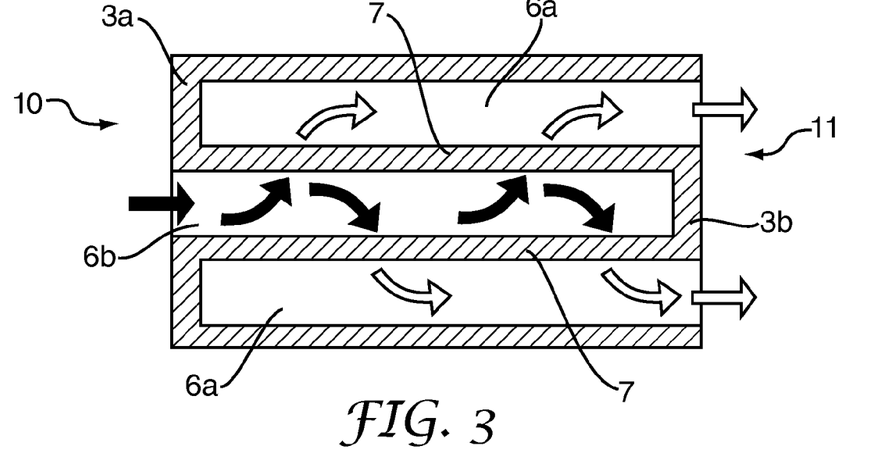
FIG. 3 is a diagrammatic section of part of the filter of FIG. 1, showing gas flow through the filter.

FIGS. 1 and 2 show a schematic diagram of a wall-flow filter 1 comprising a cylindrical ceramic monolith core 2 contained within a cylindrical metal surround or sleeve 4. The overall diameter of a filter 1 for a vehicle exhaust system is generally between 100 and 400 mm. The ceramic filter cores 2 have a number of elongate channels 6 running along their length. These channels 6 generally have an approximately square cross-section and are about 0.6-2 mm in width. In FIG. 1 the relative size of the channels 6 compared to the dimensions of the filter 1 has been increased for clarity. Between the channels 6 the walls 7 of the filter core 2 are formed from a porous ceramic. The ceramic may be, for example, cordierite (magnesium iron aluminium cyclosilicate), silicon carbide, or aluminium titanate. Typical porosities are between 40 and 50% with a mean pore size between 10 and 20 μm, or smaller for Euro 6 filters. Neighbouring channels 6 in the filter 1 are plugged at alternate ends with plugs 3a, 3b (FIG. 3) of a ceramic material so that exhaust gases entering a channel 6 at one end 6b cannot exit the same channel 6b at its other end. To exit, the gas must pass from one channel 6b to the next 6a through the porous walls 7 of the filter 1. The metal sleeve 4 of the filter 1 includes flanges 8 at each end which, when in use, aid the connection of the filter 1 to other parts of a vehicle's exhaust system. In the embodiment shown in FIG. 1, the flanges 8 usually extend outwards at an angle from the top and bottom edges of the cylindrical sleeve 4. However, the flanges may be of a different design to accept a variety of fittings.

When installed in a vehicle exhaust system, typically an exhaust system of a diesel engine, the exhaust gases flow through the filter 1 from a first end 10 to a second end 11. Particulate matter therefore builds up in those channels 6 having their open ends at the first end 10 of the filter. Because the particulate matter, typically soot and ash, is trapped and removed from the gas stream by the porous ceramic walls 7, the channels 6 having open ends at the second end 11 of the filter are generally significantly cleaner than the other channels 6.

The wall-flow filter 1 typically would be used in a heavy-duty diesel-powered vehicle. Over time, the filter 1 will become contaminated with the soot and ash that is filtered from the exhaust stream. A CR-DPF is designed such that heat from the vehicle exhaust causes the filter to self-clean by nitrogen dioxide reacting with the soot to 'burn' it off the filter. However, under adverse conditions, for example if the vehicle exhaust does not routinely reach sufficiently high temperatures, or after prolonged use, the filter, or one or more channels of the filter, can become blocked. This can cause an exothermic reaction which burns the material of the filter. Blockages and/or the subsequent damage to the filter material, can damage the integrity of the filter and impair its performance.

Figure 4:
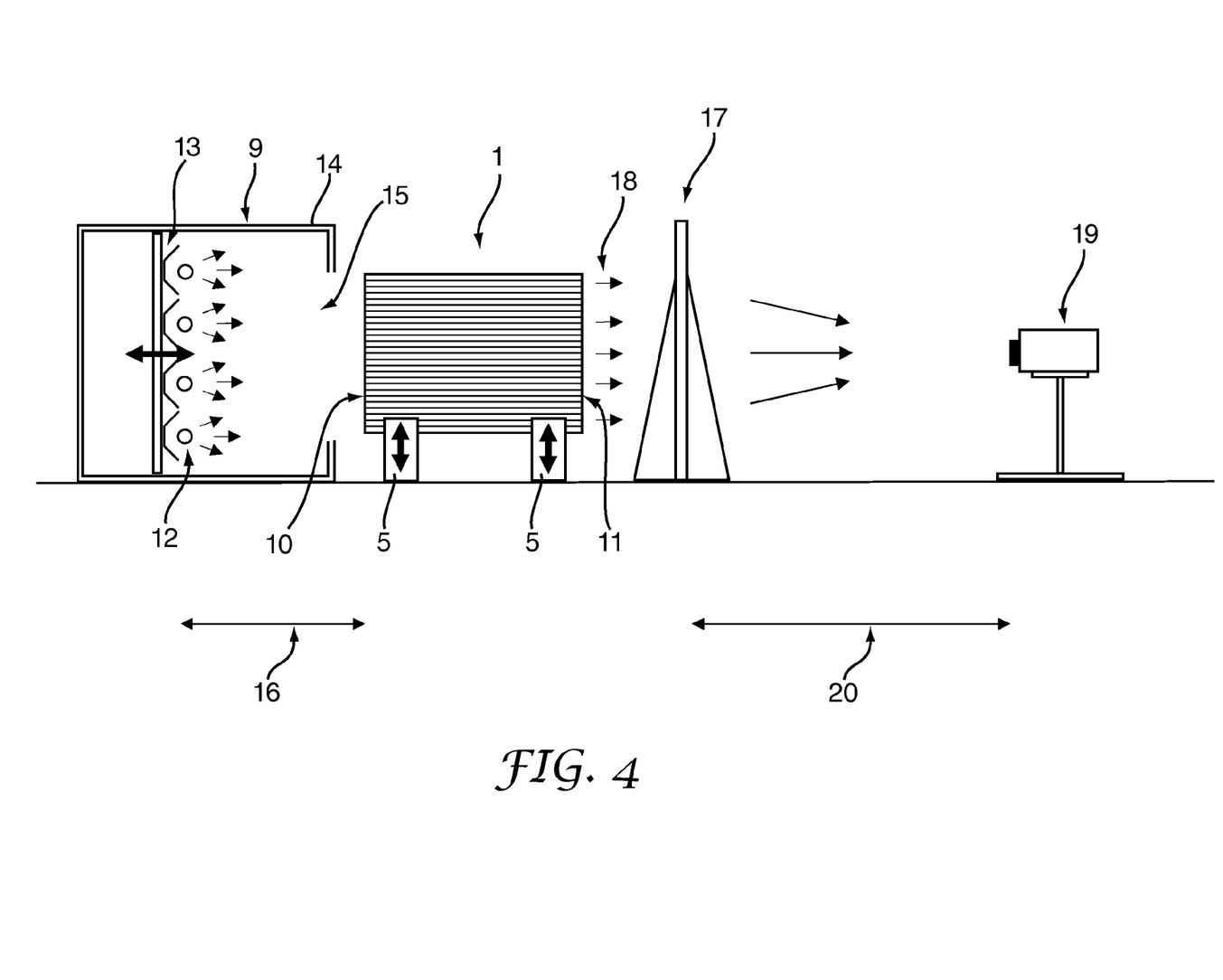
FIG. 4 is a diagrammatic view of apparatus for use in an embodiment of the present invention.

Referring now to FIG. 4, apparatus for use in accordance with an embodiment of the invention is illustrated. A filter 1, in this example a CR-DPF, is mounted on height-adjustable legs 5, with a first end 10 facing a heat energy source 9. In this example, the heat energy source 9 comprises one or more infrared lamps 12 in a housing 14 having a window opening 15 which faces the first end 10 of the filter 1. Each of the lamps 12 is preferably provided with a reflector 13 to enhance emission of radiation out through the window 15. Preferably the infrared source emits at peak wavelengths in the range 0.9 to 3 μm. In one embodiment we have used as infrared lamps, 4×1500 W Ruby coloured lamps which emit infrared at wavelengths between about 0.7 and 7 μm, with about 90% of the energy in the range 0.9 to 2 μm and with an emission peak at about 1.2 μm. The lamps are backed with reflectors that both reflect this radiation and also become hot themselves (up to about 100° C.) and in doing so emit further low level radiation at longer wavelengths. Radiation from the heat energy source 9 is applied to the first end 10 of the filter 1. The incident radiation is absorbed by the core of the filter 1 and initially no detectable radiation is emitted from the second end 11 of the filter 1. After some time, typically 10 to 50 seconds, material within the filter 1 that has been heated by the incident radiation, becomes sufficiently hot to emit infrared radiation 18 that emerges from the second end 11 of the filter. The emitted infrared radiation 18 in this example is focused by a Fresnel lens 17 and directed to a thermal imaging camera 19 spaced apart from the lens 17 by about the distance of the focal length 20 of the lens 17. In this embodiment the electromagnetic radiation emitted by the source 9 is infrared radiation; however, other wavelengths may also be used, for example microwave radiation. Preferred radiation types are longer wavelength IR or shorter wavelength microwave.

Without wishing to be bound by theory, we believe that what happens is that the incident radiation is absorbed by and selectively heats the end plugs 3a and cell walls 7 of the first (hot) end 10 of the filter 1. The heated surfaces radiate 'black body' radiation, typically at a different wavelength and higher intensity than the radiation emitted by other parts of the filter. Emitted radiation is partially collimated by the length of the channel and exits at the second (cold) end 11 of the filter 1. The thermal imaging camera 19 is most sensitive in the waveband 7 to 14 μm and receives focused IR radiation from both cold and hot faces of the filter. The cold face is at ambient temperature while the hot face typically reaches about 40° C. before an image of good contrast is obtained. Radiation from the inside edge of the hot face has to pass through the length of the cell before being collected by the lens. In doing so, much radiation is believed to be reabsorbed into the substrate along its path, limiting the amount for detection and slowly raising the temperature in the rest of the filter. As heat is continually applied to the hot face, the thermal gradient along the filter continues to rise.

Any blockage within the channels (cells) open to the cold end acts as a heat sink and results in a lower temperature being observed. With time, the blockage will start to warm up and emit infrared radiation. A blockage closer to the hot end will heat up more quickly than one nearer to the cold end, providing the possibility of obtaining an approximation of the depth of the blockage by measuring the change in appearance of the blockage area over a fixed time period. Information about blockages in the channels 6 which are open at the first end may be obtained by turning the filter around so that the previous cold end is near the radiation source 9 and the previous hot end is near the lens 17. The method allows a three-dimensional image of the filter and its blockages to be constructed.

Whether a filter is acceptably clean may be determined according to whether a filter passes or fails an acceptability criterion. The criterion may depend on whether the number or percentage of blocked channels in the filter, determined by observation of the pattern of emitted radiation, exceeds a preset threshold value. For example, if the threshold is set at 10%, and observation of the thermal image shows that 15% of channels have a blockage, the result would be a FAIL, and the filter cleaning would be deemed unacceptable.

Figure 5:
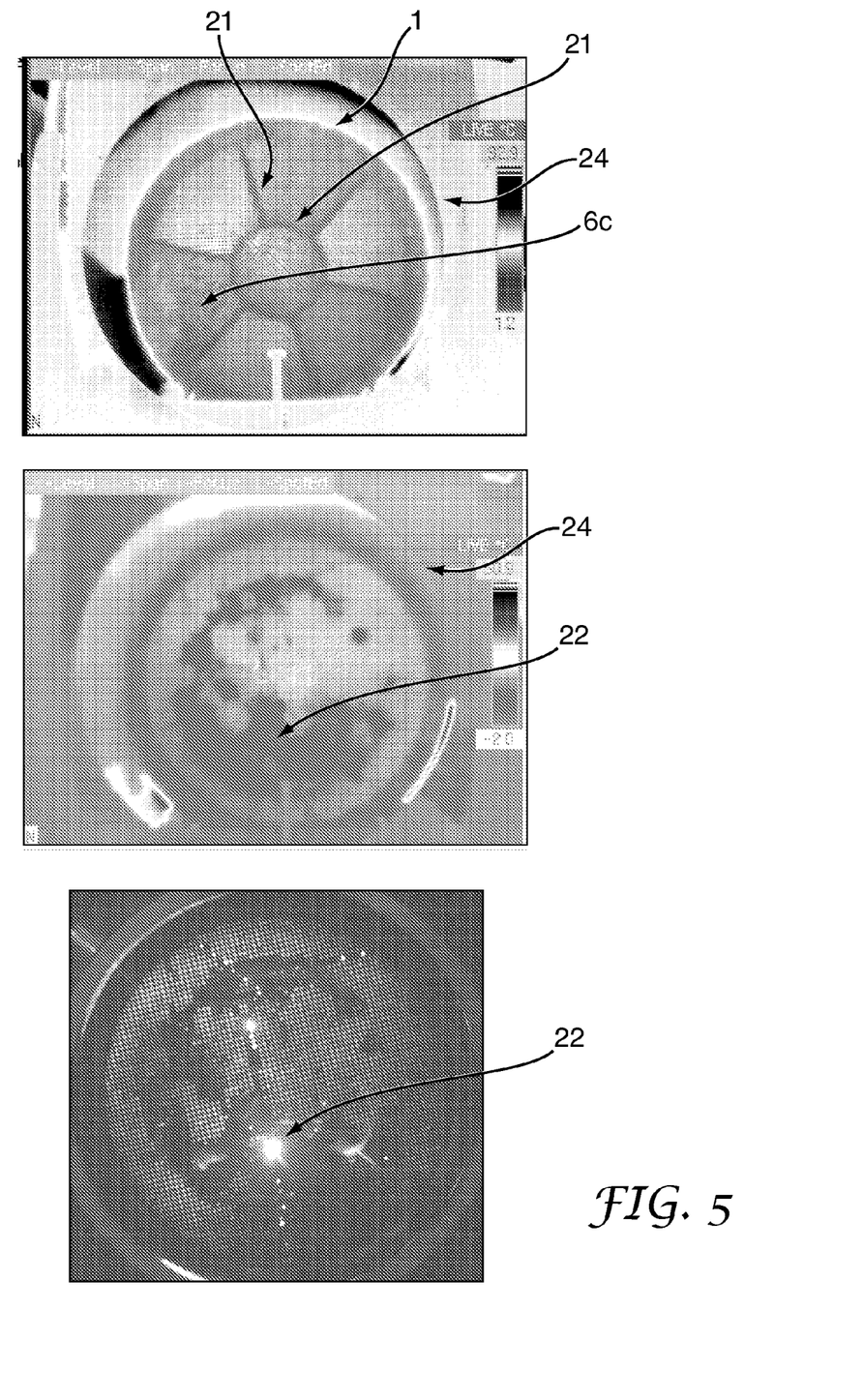
FIG. 5 shows infrared and visible light images of sample filters.

The top picture of FIG. 5 shows a thermal image (24) of a silicon carbide filter prepared in accordance with an aspect of the invention. The filter 1 was irradiated with infrared radiation from IR radiant lamps having a total power of 3 kW. The lamps emit radiation around the 2.2 μm wavelength and raise the surface temperature of the filter by 20-25° C. in one minute. Typically, about 30 s heating was required to obtain a thermal image with good contrast. After a time delay, the image of emitted radiation was captured by a thermal imaging camera. As can readily be seen, the filter 1 comprises six segments arranged around a central core. The cement lines 21 are readily visible. One segment has some partially blocked channels 6c which show up as darker regions. Attempts to view this filter using transmitted light of various wavelengths were unsuccessful.

The middle picture of FIG. 5 was made using the same method as for the top image. The filter was a CRT-type cordierite filter. The image (24) shows blocked cells due to extensive exotherm damage in region 22. By way of comparison, the bottom image of FIG. 5 shows the same filter when illuminated from behind with white light and imaged through a standard camera.

Figure 6:
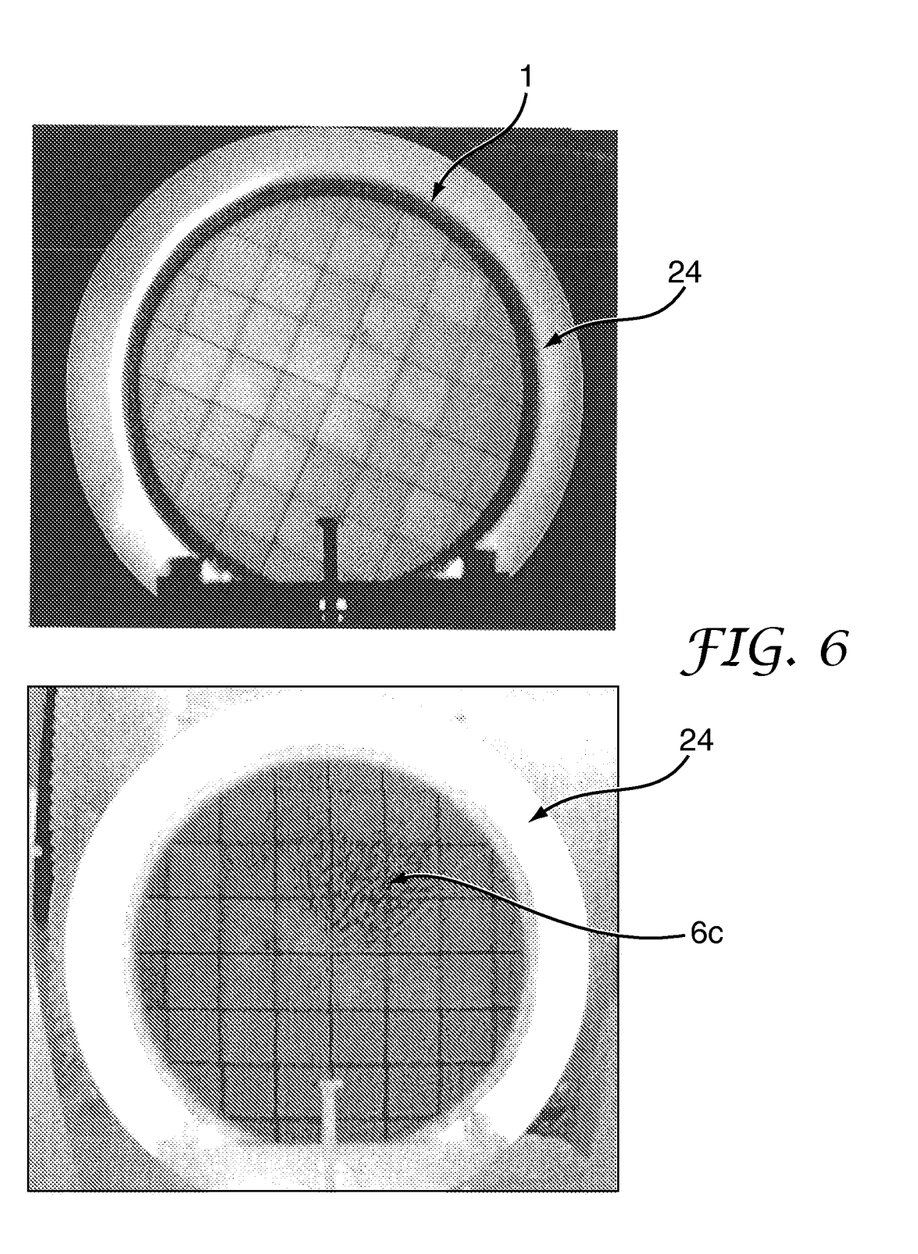
FIG. 6 shows infrared images of sample filters and a filter support used in a cleaning process.

Referring now to FIG. 6, greyscaled infrared images (24) of a silicon carbide filter are shown. The upper image shows a clean filter. In the lower image, the previously clean filter has had some channels partially blocked with powdered ash and soot. The partially blocked channels 6c are clearly visible.

Figure 7A:
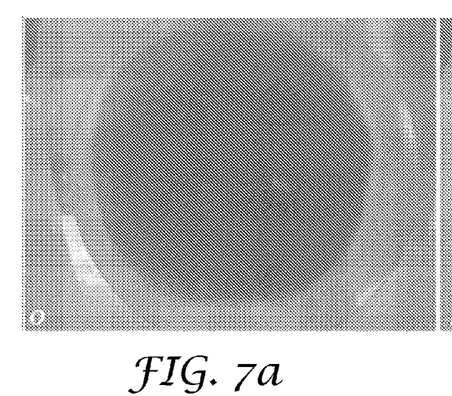
FIG. 7 shows a series of infrared images of patterns of emitted infrared radiation from a filter, taken at a plurality of time intervals, for use in a method according to an aspect of the invention.
Figure 7B:
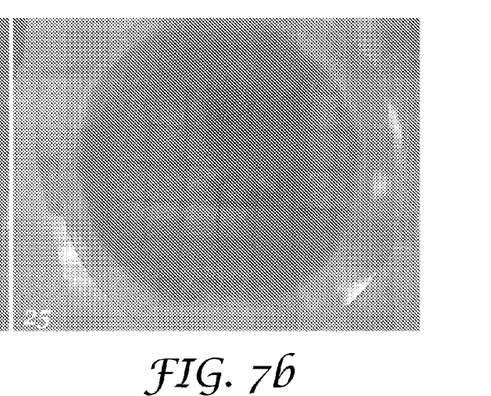
Figure 7C:
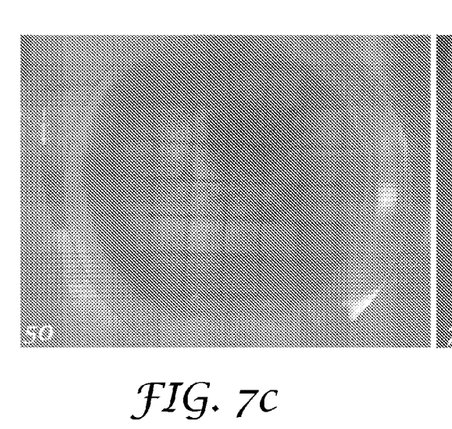
Figure 7D:
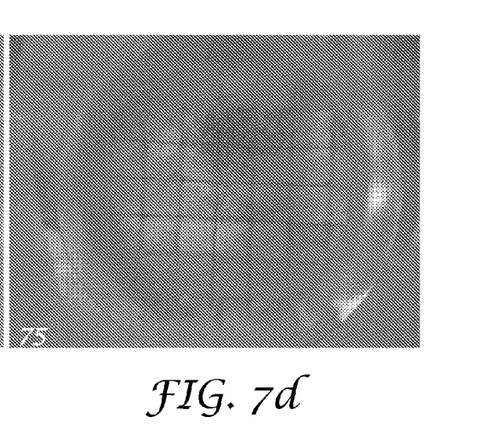
Figure 7E:
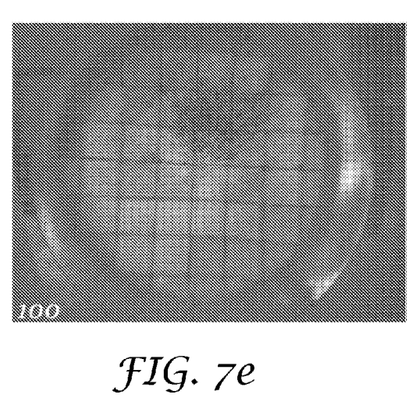
Figure 7F:
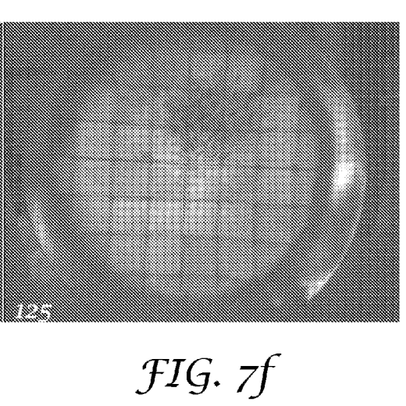
Figure 7G:
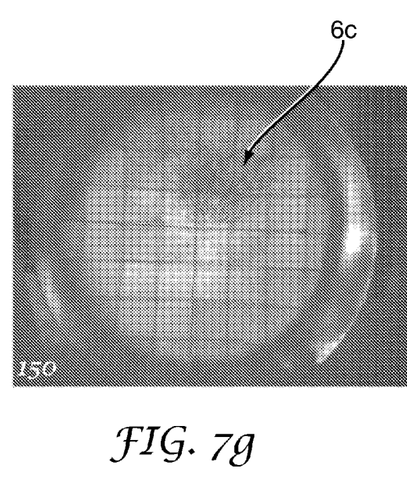
Figure 7H:
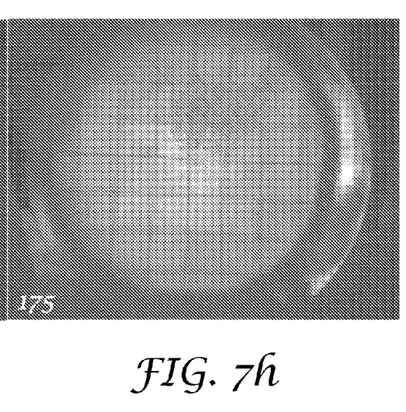
Figure 7I:
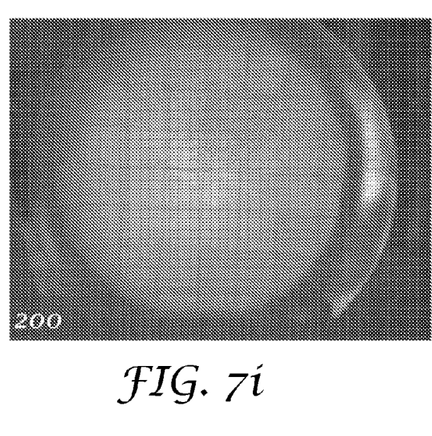
Figure 7J:
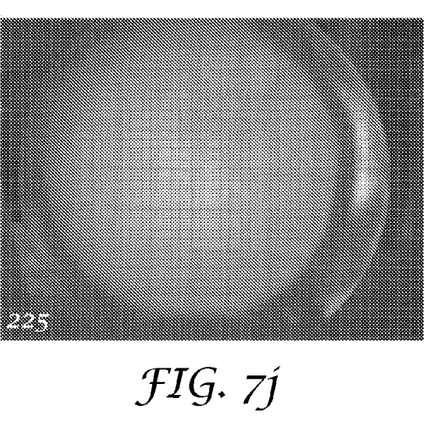
Figure 7K:
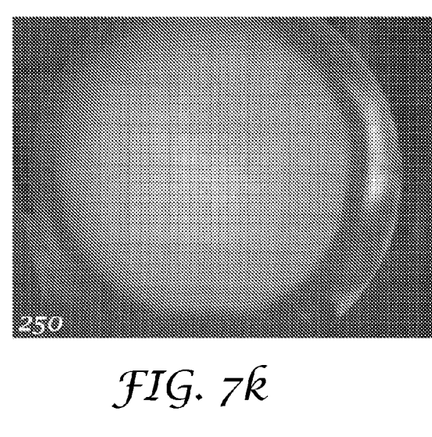
Figure 7L:
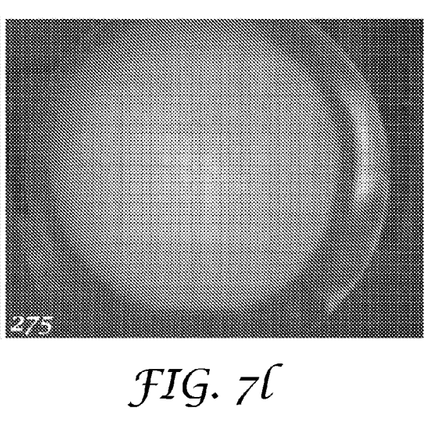
Figure 7M:
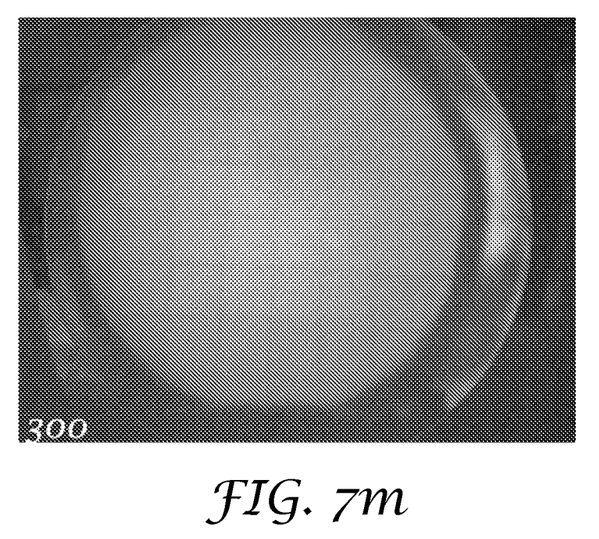
Figure 7N:
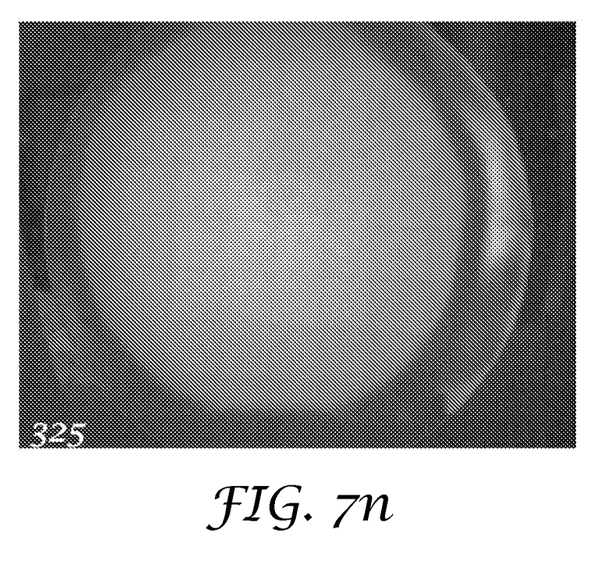

FIGS. 7a-7n show a sequence of thermal images taken of the silicon carbide filter of FIG. 6. The time interval (seconds) from initial application of infrared radiation is given in the bottom left hand corner of each image. Beginning at time zero (FIG. 7a) the thermal image is indistinguishable. After about 25 seconds (FIG. 7b) the face of the filter and the blocked cells start to become visible. From about 100 s (FIG. 7e) to 150 s (FIG. 7g) the image contrast is at its highest, with the blocked cells 6c clearly visible. Further irradiation results in more generalised heating, and the image gradually loses contrast.

Depending on the location of the blockage, we expect that the image will take more or less time to develop. A blockage close to the 'hot' face of the filter is expected to heat up more quickly, while a blockage closer to the 'cold' face is expected to take longer to heat up. Hence, measuring the time for an image of a blockage to fade through being heated to a given degree affords an indication of the depth of the blockage. By carrying out a similar measurement of the same blockage using heat energy, for example electromagnetic radiation, applied from the other end of the filter, three dimensional information about the blockage may be obtained. Heating times will also depend on factors such as the nature and power of the electromagnetic radiation, the amount of radiation that is coupled with the face of the filter, and the composition of the filter material and dimensions of the channels. Blockage depth may be measured directly using other means, for example by measuring the depth to which a metal rod can be inserted into a channel. Such measurements may be used to calibrate the method by relating the measured imaging times to the known blockage depth.

As an alternative source of electromagnetic radiation to cause heating of the material of the filter, we propose to use a heated metal plate, notably a blackened copper plate heated to a temperature of a few hundred degrees Celsius by embedded electrical elements. An advantage of this arrangement is that it can provide very uniform heating of the filter surface by longer wavelength radiation over a much broader spectrum. Much of the radiation emitted by the black body will be in the 7 to 14 μm range, matching the sensitivity of the thermal imaging camera. This is expected significantly to improve the detection of damage within filters as the camera will be better attuned to the wavelength of the source radiation. Although most of the heat energy applied to the first end is not transmitted through the second end, because it is absorbed, damaged areas of a filter plug will allow some transmission of the heat energy to the other end. Damaged areas should thus show brightly on the image as hot spots.

It will be understood that the terms "first end" and "second end" are used herein for convenience, and that the method may be used with either end of the filter as the hot face, and that each end of the filter may in turn be used as the hot face, providing different information about the length and location of blockages and allowing a 3-D image to be created.

The invention claimed is:

1. A method of inspecting a ceramic wall-flow filter for a vehicle exhaust system, the filter having a first end and a second end; the method including the steps of:
   a) providing a source of heat energy suitable for heating material within the filter;
   b) applying heat energy from the source to the first end of the filter to heat material within the filter;

c) detecting infrared radiation which has been emitted by heated material in the filter using a radiation detector at the second end of the filter to form an image of a pattern of emitted radiation, the pattern of emitted radiation providing an indication of the condition of the filter;

wherein the applied heat energy has an emission peak wavelength which is substantially different from the emission peak wavelength of the emitted radiation detected by the radiation detector.

2. A method according to claim 1, wherein the heat energy applied to the first end of the filter is substantially not transmitted through the second end.

3. A method according to claim 1, wherein the step of forming an image is carried out at a plurality of time intervals, producing a plurality of images.

4. A method according to claim 3, wherein the plurality of images is obtained during a period of from 5 to 300 seconds from the application of the heat energy to the first end of the filter.

5. A method according to claim 3, wherein at least some of the images have a different contrast than others without the intensity of applied heat energy having substantially changed.

6. A method according to claim 3, wherein the plurality of images is obtained during a period of from 15 to 60 seconds from the application of the heat energy to the first end of the filter.

7. A method according to claim 1, further comprising the steps of ceasing to apply the heat energy to the first end of the filter, applying heat energy to the second end of the filter, and detecting infrared radiation which has been emitted by heated material using a radiation detector at the first end of the filter to form an image of a pattern of emitted radiation, the pattern of emitted radiation providing an indication of the condition of the filter.

8. A method according to claim 7, wherein the step of forming an image is carried out at a plurality of time intervals, producing a plurality of images.

9. A method according to claim 7, further comprising the step of determining the position or length of a blockage within a channel of the filter from the time taken for each thermal image corresponding the blockage to develop or fade.

10. A method according to claim 1, further comprising the step of determining the position or length of a blockage within a channel of the filter from the time taken for a thermal image corresponding the blockage to develop or fade.

11. A method according to claim 1, further comprising the step of determining whether a filter passes or fails an acceptability criterion depending on whether the number or percentage of blocked channels in the filter, determined by observation of the pattern of emitted radiation, exceeds a preset threshold value.

12. A method according to claim 1, wherein the applied heat energy has an emission peak wavelength in the range 0.9 to 3 μm and the emitted radiation has a peak wavelength in the waveband range 7 to 14 μm.

13. A method according to claim 1, wherein the ceramic material of the filter is silicon carbide.

14. A method according to claim 1, wherein the ceramic material of the filter carries a catalytic coating.

15. A method according to claim 14, wherein the ceramic material is selected from the group comprising cordierite, silicon carbide and aluminum titanate.

16. Apparatus for use in the method of claim 1, the apparatus comprising:
a) a source of heat energy suitable for heating material within a ceramic wall-flow filter for a vehicle exhaust system;
b) means for mounting the filter such that heat energy when emitted from the source will heat at least a part of a first end of the filter to a temperature such that infrared radiation radiated by heated material in the filter may form an image of a pattern of emitted radiation;
c) a radiation detector capable of forming an image of a pattern of radiation emitted by heated material in the filter, the pattern of emitted radiation providing an indication of the condition of the filter;

wherein the heat energy, when emitted from the source to a filter, has an emission peak wavelength which is substantially different from the emission peak wavelength of the emitted radiation when detected by the radiation detector.

17. Apparatus according to claim 16, wherein the heat source has a power output per unit area of at least 10 kW·m$^{-2}$.

18. Apparatus according to claim 16, wherein the source of heat energy is arranged and adapted to raise the temperature of at least a part of a first end of the filter by at least 20° C.

19. Apparatus according to claim 16, wherein the heat source has a power output per unit area of 10 to 20 kW·m$^{-2}$.

* * * * *